United States Patent

Yamaguchi et al.

Patent Number: 6,031,131
Date of Patent: Feb. 29, 2000

[54] FLUORINATED AMIDE COMPOUNDS

[75] Inventors: Kouichi Yamaguchi; Noriyuki Koike; Hirofumi Kishita; Masatoshi Arai, all of Gunma-ken, Japan

[73] Assignee: Shin-Etsu Chemical Co., Ltd., Tokyo, Japan

[21] Appl. No.: 09/158,574

[22] Filed: Sep. 22, 1998

[30] Foreign Application Priority Data

Sep. 22, 1997 [JP] Japan ................................. 9-275022

[51] Int. Cl.[7] .................................................. C07C 233/05
[52] U.S. Cl. ........................... 564/153; 564/157; 564/159
[58] Field of Search ................................. 564/153, 157, 564/159; 544/359; 546/189

[56] References Cited

FOREIGN PATENT DOCUMENTS 4322851 1/1995 Germany .

OTHER PUBLICATIONS

Fokin et al, Izv. Akad. Nauk SSSR, Ser Khim, vol. 38, No. 2, part 2, pp. 329–332, 1989.

*Primary Examiner*—Shailendra Kumar
*Attorney, Agent, or Firm*—Birch, Stewart, Kolasch & Birch, LLP

[57] ABSTRACT

The invention is directed at novel fluorinated amide compounds of formula (1):

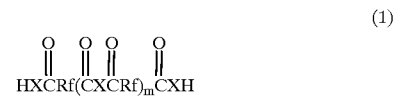

(1)

wherein Rf is a divalent perfluoroalkylene or perfluoropolyether group, X is a group of formula (2), (3) or (4), and m is an integer inclusive of 0.

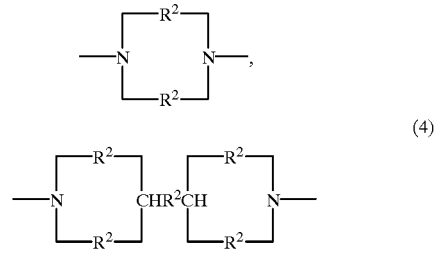

$R_1$ is a monovalent hydrocarbon group, and $R^2$ is a divalent hydrocarbon group. These compounds can be used to obtain elastomers or cured resins having a high fluorine content and a low surface energy, making them effective as starting materials in the production of chemical and isolvent-resistant elastomeric materials, parting agents, and water repellents.

1 Claim, 3 Drawing Sheets

FLUORINATED AMIDE COMPOUNDS

BACKGROUND OF THE INVENTION

1. Field of the Invention

The present invention relates to novel fluorinated amide compounds which are useful as starting materials in the production of, for instance, elastomeric materials having solvent and chemical resistance, parting agents, and water repellents.

2. Prior Art

Organic fluorine compounds are used in many areas of application. For example, polymers of organic fluorine compounds are crosslinked using crosslinking agents to give fluorinated elastomers and cured resins, which are employed as elastomeric materials, coatings, parting agents, and water repellents.

However, because prior-art fluorinated elastomers and cured resins generally do not have sufficient solvent resistance and chemical resistance, a need has been felt for fluorinated elastomers and cured resins having better resistance to solvents and chemicals. There has also been felt a need for fluorinated elastomers and cured resins used as coatings, parting agents, water repellents and the like which have, in addition, excellent release characteristics and water repellency.

It is, therefore, an object of the present invention to provide novel fluorinated amide compounds which can form fluorinated elastomers and cured resins having excellent resistance to solvents and chemicals, and also outstanding release characteristics and water repellency.

SUMMARY OF THE INVENTION

We have found that compounds of general formula (5) below having at both ends acid fluoride groups can be reacted with secondary amine compounds of general formula (6) to form novel fluorinated amide compounds of general formula (1) which can in turn form elastomers having a high fluorine content and a low surface energy. Hence, these novel fluorinated amide compounds of general formula (1) can be used to obtain fluorinated elastomers and cured resins having excellent solvent and chemical resistance, and also outstanding release characteristics and water repellency.

$$FOC-Rf-COF + H-X-H$$
$$(5) \quad\quad\quad (6)$$

↓

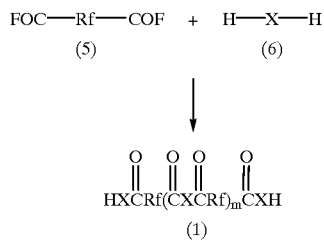

(1)

In the above formulas, Rf is a divalent perfluoroalkylene or divalent perfluoropolyether group; X is a group represented by general formula (2), (3) or (4); and the letter m is an integer inclusive of 0.

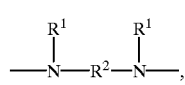

(2)

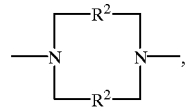

(3)

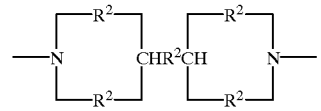

(4)

$R^1$ is a substituted or unsubstituted monovalent hydrocarbon group, and $R^2$ is a substituted or unsubstituted divalent hydrocarbon group.

DETAILED DESCRIPTION OF THE INVENTION

Figure 1:
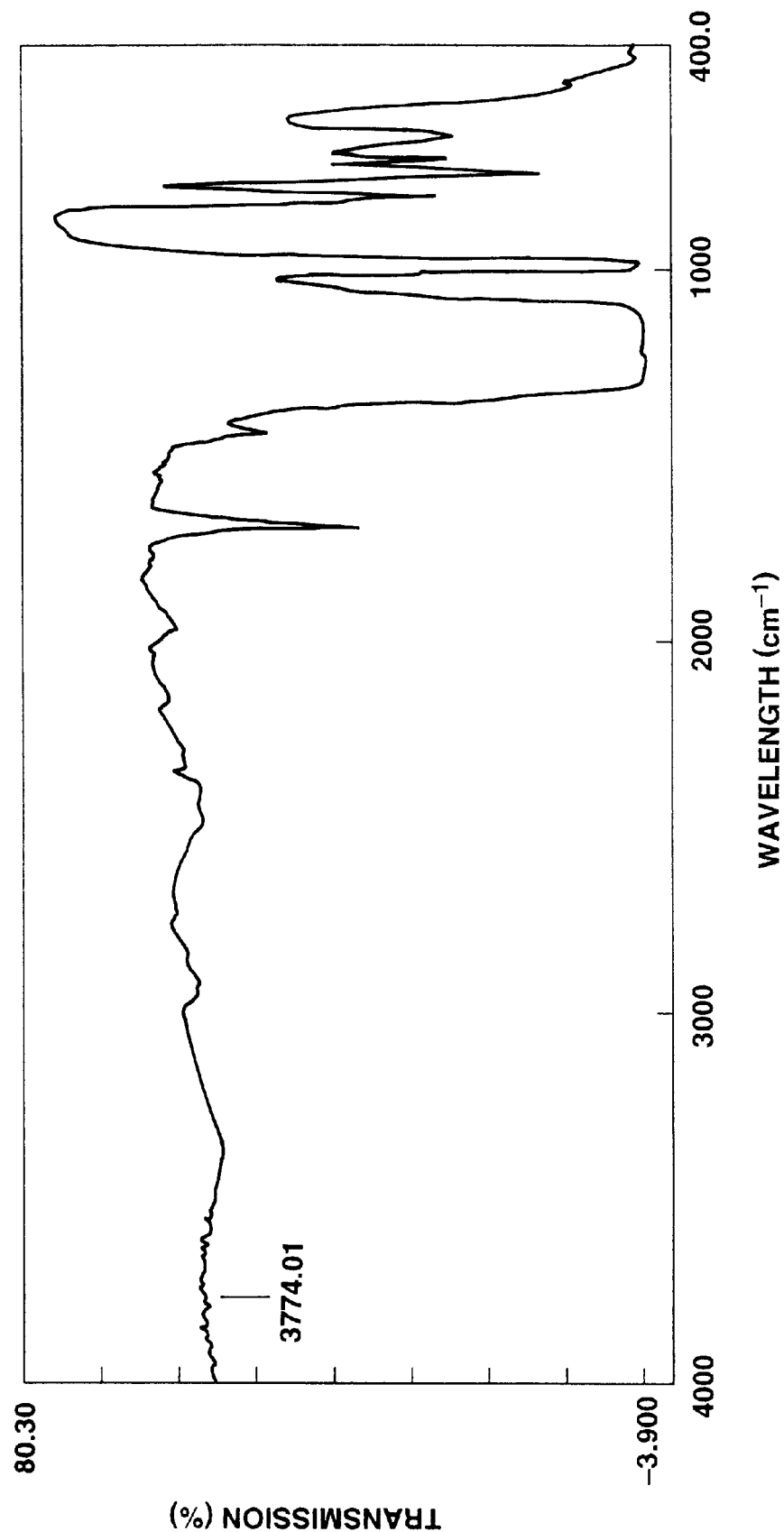
FIG. 1 shows the IR absorption spectrum measured for the fluorinated amide compound obtained in Example 1.

The fluorinated amide compounds of this invention have the following general formula (1).

(1)

Rf is a divalent perfluoroalkylene or divalent perfluoropolyether group; X is a group represented by general formula (2), (3) or (4); and the letter m is an integer inclusive of 0.

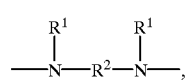

(2)

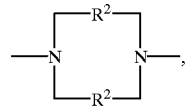

(3)

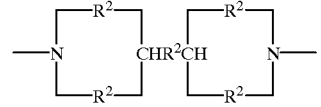

(4)

$R^1$ is a substituted or unsubstituted monovalent hydrocarbon group, and $R^2$ is a substituted or unsubstituted divalent hydrocarbon group.

In formula (1), Rf is a divalent perfluoroalkylene group or a divalent perfluoropolyether group. The divalent perfluoroalkylene group is preferably of the formula: $-C_nF_{2n}-$ wherein n is 1 to 10, and especially 2 to 6. The divalent perfluoropolyether group preferably has one of the following formulas:

$$-(\underset{\underset{Y}{|}}{CFOCF_2})_p(CF_2)_r(\underset{\underset{Y}{|}}{CFOCF})_q-$$

wherein Y is fluorine or a $CF_3$ group, and p, q, and r are integers in the ranges $p \geq 1$, $q \geq 1$, $2 \leq p+q \leq 200$, and especially $2 \leq p+q \leq 100$, and $0 \leq r \leq 6$;

$$-CF_2CF_2OCF_2(\underset{\underset{CF_3}{|}}{CFOCF_2})_s(CF_2)_r(CF_2O\underset{\underset{CF_3}{|}}{CF})_tCF_2OCF_2CF_2-$$

wherein r, s, and t are integers in the ranges $0 \leq r \leq 6$, $s \geq 0$, $t \geq 0$, and $0 \leq s+t \leq 200$, and especially $2 \leq s+t \leq 100$;

$$-\underset{\underset{Y}{|}}{CF}(O\underset{\underset{Y}{|}}{CFCF_2})_u(OCF_2)_v O\underset{\underset{Y}{|}}{CF}-$$

wherein Y is fluorine or a $CF_3$ group, and u and v are integers in the ranges $1 \leq u \leq 100$ and $1 \leq v \leq 100$; and $$-CF_2CF_2(OCF_2CF_2CF_2)_w OCF_2CF_2-$$

wherein w is an integer in the range $1 \leq w \leq 100$.

Illustrative examples of Rf include the following groups:

$$-C_4H_8-, \quad -C_6H_{12}-,$$

$$-(\underset{\underset{CF_3}{|}}{CFOCF_2})_n(CF_2O\underset{\underset{CF_3}{|}}{CF})_m-$$

wherein n+m is from 2 to 200, $$-CF_2CF_2OCF_2(CF_2)_2CF_2OCF_2CF_2-,$$

$$-CF_2CF_2OCF_2(CF_2)_2CF_2OCF_2CF_2-,$$

$$-CF_2CF_2OCF_2\underset{\underset{CF_3}{|}}{CFOCF_2}(CF_2)_2CF_2O\underset{\underset{CF_3}{|}}{CFCF_2}OCF_2CF_2-,$$

$-CF_2(OCF_2CF_2)_n(OCF_2)_m OCF_2-$ wherein n is from 5 to 100, and m is from 1 to 100, $$-\underset{\underset{CF_3}{|}}{CF}(O\underset{\underset{CF_3}{|}}{CFCF_2})_n(OCF_2)_m O\underset{\underset{CF_3}{|}}{CF}-,$$

wherein n is from 5 to 100, and m is from 1 to 100, and $-CF_2CF_2(OCF_2CF_2CF_2)_n OCF_2CF_2-$ wherein n is from 5 to 100.

In formula (1), X is a group represented by general formula (2), (3) or (4).

$$-\underset{\underset{R^1}{|}}{N}-R^2-\underset{\underset{R^1}{|}}{N}-, \quad (2)$$

$$-N\underset{\underset{R^2}{\diagdown}}{\overset{\overset{R^2}{\diagup}}{\diagdown}}N-, \quad (3)$$

$$-N\underset{\underset{R^2}{\diagdown}}{\overset{\overset{R^2}{\diagup}}{\diagdown}}CHR^2CH\underset{\underset{R^2}{\diagdown}}{\overset{\overset{R^2}{\diagup}}{\diagdown}}N-, \quad (4)$$

In formula (2), $R^1$ represents a substituted or unsubstituted monovalent hydrocarbon group having preferably 1 to 12 carbons, and more preferably 1 to 8 carbons. Illustrative examples include alkyl groups such as methyl, ethyl, propyl, isopropyl, butyl, isobutyl, tert-butyl, pentyl, neopentyl, hexyl, heptyl, octyl, nonyl, and decyl; cycloalkyl groups such as cyclopentyl, cyclohexyl, and cycloheptyl; aryl groups such as phenyl, tolyl, xylyl, and naphthyl; aralkyl groups such as benzyl, phenylethyl, and phenylpropyl; and these groups in which some or all of the hydrogen atoms are replaced with halogen atoms (e.g., fluorine, chlorine, and bromine), such as chloromethyl, bromoethyl, chloropropyl, trifluoropropyl, and 3,3,4,4,5,5,6,6,6-nonafluorohexyl.

In formulas (2) to (4) above, $R^2$ represents a substituted or unsubstituted divalent hydrocarbon group having preferably 1 to 10 carbons, and more preferably 2 to 6 carbons. Illustrative examples include alkylene groups such as methylene, ethylene, propylene, methylethylene, butylene, and hexamethylene; cycloalkylene groups such as cyclohexylene; arylene groups such as phenylene, tolylene, xylylene, naphthylene, and biphenylene; and these groups in which some of the hydrogen atoms are replaced with halogen atoms such as fluorine. The two $R^2$ groups in formula (3) and the five $R^2$ groups in formula (4) may, respectively, be mutually like or unlike.

Illustrative examples of the secondary amino group of formula (2), (3) or (4) represented by X in formula (1) include the groups shown below, wherein Me stands for methyl and Ph stands for phenyl.

$$-\underset{\underset{Me}{|}}{N}(CH_2)_2\underset{\underset{Me}{|}}{N}-, \quad -\underset{\underset{Ph}{|}}{N}(CH_2)_2\underset{\underset{Ph}{|}}{N}-,$$

$$-N\underset{\underset{CH_2CH_2}{\diagdown}}{\overset{\overset{CH_2CH_2}{\diagup}}{\diagdown}}N-, \quad -N\underset{\underset{\underset{\underset{Me}{|}}{CHCH_2}}{\diagdown}}{\overset{\overset{CH_2CH}{\diagup}}{\diagdown}}N-,$$

$$-\underset{\underset{Me}{|}}{N}CH_2-\phantom{O}\!\!\!\!\!\bigcirc\!\!\!\!\!\phantom{O}-CH_2\underset{\underset{Me}{|}}{N}-,$$

$$-\underset{\underset{Ph}{|}}{N}-\phantom{O}\!\!\!\!\!\bigcirc\!\!\!\!\!\phantom{O}-\phantom{O}\!\!\!\!\!\bigcirc\!\!\!\!\!\phantom{O}-\underset{\underset{Ph}{|}}{N}-,$$

$$-\underset{\underset{Me}{|}}{N}-\phantom{O}\!\!\!\!\!\bigcirc\!\!\!\!\!\phantom{O}-CH_2-\phantom{O}\!\!\!\!\!\bigcirc\!\!\!\!\!\phantom{O}-\underset{\underset{Me}{|}}{N}-,$$

-continued

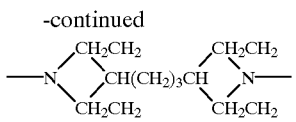

The letter m in above formula (1) is an integer inclusive of 0, preferably an integer from 0 to 10, and more preferably an integer from 0 to 6. Accordingly, the fluorinated amide compound of formula (1) contains at least one divalent perfluoroalkylene group or divalent perfluoropolyether group per molecule.

The fluorinated amide compounds of formula (1) according to the invention encompass compounds ranging from low-viscosity polymers having a viscosity within a range of about 100 to about 100,000 centistokes (cs) at 25° C. to solid, crude rubber-like polymers. For reasons having to do with the ease of handling, crude rubber-like polymers are preferred in the production of hot-vulcanized rubber,, for example, whereas polymers having a viscosity within a range of about 100 to 100,000 cs at 25° C. are preferred in the production of liquid rubber. A compound having a viscosity of less than 100 cs at 25° C. may cure into a product which has a two low elongation for an elastomer, and thus fails to achieve a good balance of physical properties.

The fluorinated amide compound of formula (1) can be synthesized by the following method. As shown by the following scheme, a compound of general formula (5) having acid fluoride groups at both ends is reacted with a secondary diamine compound of general formula (6), optionally in the presence of an acid acceptor such as trimethylamine.

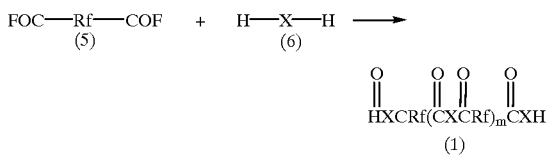

X, Rf, and m are as defined above.

No particular limit is imposed on the proportions in which the compound of formula (5) having acid fluoride groups at both ends and the secondary diamine compound of formula (6) are charged in the above method, although the molar ratio (a)/(b) between the number of moles (a) of the formula (5) compound charged to the number of moles (b) of the formula (6) compound charged is preferably from 0.05 to 1, and more preferably from 0.1 to 0.5. The number (m) of repeating units in formula (1) can be set to a value suitable for the intended purpose by adjusting the ratio (a)/(b). For example, relatively low-molecular-weight polymers can be synthesized by making the (a)/(b) ratio small, and high-molecular-weight polymers can be synthesized by bringing the ratio closer to 1.

When the above reaction is carried out, the components may be diluted with an organic solvent, provided the solvent has no influence on the reaction. The use of an organic solvent in which the components and the reaction product can be dissolved or uniformly dispersed is of considerable advantage for enabling the reaction to proceed smoothly. Examples of suitable organic solvents include hydrocarbon solvents such as n-hexane, cyclohexane, toluene, petroleum ether, and xylene; ether-type solvents such as diethyl ether, n-butyl ether, dioxane, and tetrahydrofuran; ketone-type solvents such as acetone, methyl ethyl ketone, dibutyl ketone, and ethyl acetate; chlorohydrocarbon solvents such as methylene chloride, chlorobenzene, and chloroform; nitrile solvents such as acetonitrile; and fluorocarbon solvents such as trifluorobenzene, 1,3-bistrifluoromethylbenzene, and perfluorooctane. These solvents may be used alone or as mixtures of two or more thereof, if necessary.

Although the reaction conditions are not critical, the reaction is preferably carried out at a temperature of about 20 to 150° C. for a period of about 1 to 8 hours, and more preferably at about 20 to 100° C. for about 2 to 5 hours.

The fluorinated amide compounds of the invention are able to form elastomers and cured resins having a high fluorine content and a low surface energy. Hence, they can be advantageously employed in a variety of applications as starting materials in the production of, for example, elastomeric materials with solvent and chemical resistance, parting agents, and water repellents.

An elastomer can be obtained by reacting a polymer of the inventive fluorinated amide compound having secondary amino groups at both ends with a compound having at least three epoxy groups per molecule. This elastomer has a high fluorine content and excellent resistance to chemicals and solvents. Owing to low surface energy, it also has excellent release characteristics and water repellency. These properties enable the effective use of the elastomer in such applications as sealants, molded parts, extruded parts, coating materials, parting agents, and water repellents.

EXAMPLE

The following examples are provided to illustrate the invention, and are not intended to limit the scope thereof. In the formulas given below, Me designates a methyl group.

Example 1

Piperazine (16 g) and 400 g of 1,3-bistrifluoromethylbenzene were charged into a 2-liter, four-necked flask fitted with a stirrer, a thermometer, a Dimroth condenser, and a dropping funnel, following which the temperature was raised to 80° C. under stirring. A mixture of 500 g of the compound with acid fluoride groups at both ends represented by formula (7) below and 500 g of 1,3-bistrifluoromethylbenzene was then added dropwise from the dropping funnel at a temperature of 80 to 90° C.

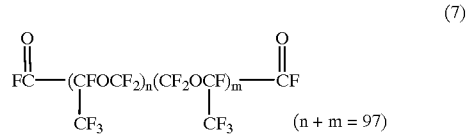

After addition, the reaction was carried out at 80° C. for 2 hours. The resulting reaction product was washed with water to remove salts and excess piperazine. The organic phase was separated off, then vacuum stripped at 100° C. and 3 mmHg, giving 467.4 g of a clear, light-yellow liquid compound.

This compound had a viscosity of 30,160 cs at 25° C. and a refractive index of 1.3073 at 25° C. The IR spectrum of this compound is shown in FIG. 1, from which the following absorption was confirmed.

| | |
|---|---|
| 1100 + 1350 cm$^{-1}$ | vC—F |
| 1710 cm$^{-4}$ | vC=O |

The functional group equivalent weight of this compound was quantitatively determined and found to be 15,725 g/mol, thereby confirming the compound to be a polymer of the fluorinated amide compound having structural formula (8) below.

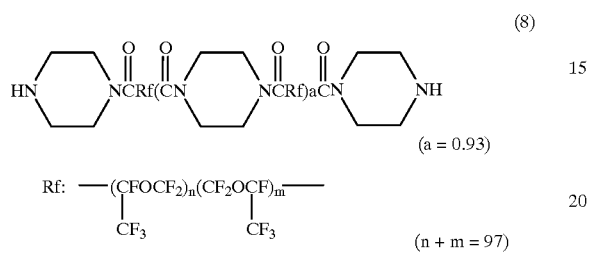

(8)

(a = 0.93)

(n + m = 97)

Example 2

2-Methylpiperazine (31.5 g) and 400 g of 1,3-bistrifluoromethylbenzene were charged into a 2-liter, four-necked flask fitted with a stirrer, a thermometer, a Dimroth condenser, and a dropping funnel, following which the temperature was raised to 80° C. under stirring. A mixture of 400 g of the compound with acid fluoride groups at both ends represented by formula (9) below and 400 g of 1,3-bistrifluoromethylbenzene was then added dropwise from the dropping funnel at a temperature of 80 to 90° C.

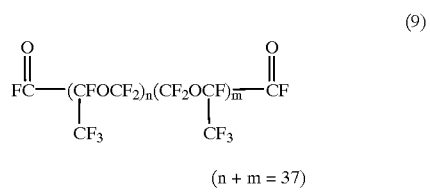

(9)

(n + m = 37)

After addition, the reaction was carried out at 80° C. for 2 hours. The resulting reaction product was washed with water to remove salts and excess 2-methylpiperazine. The organic phase was separated off, then vacuum stripped at 100° C. and 3 mmHg, giving 376.2 g of a clear, light-yellow liquid compound.

Figure 2:
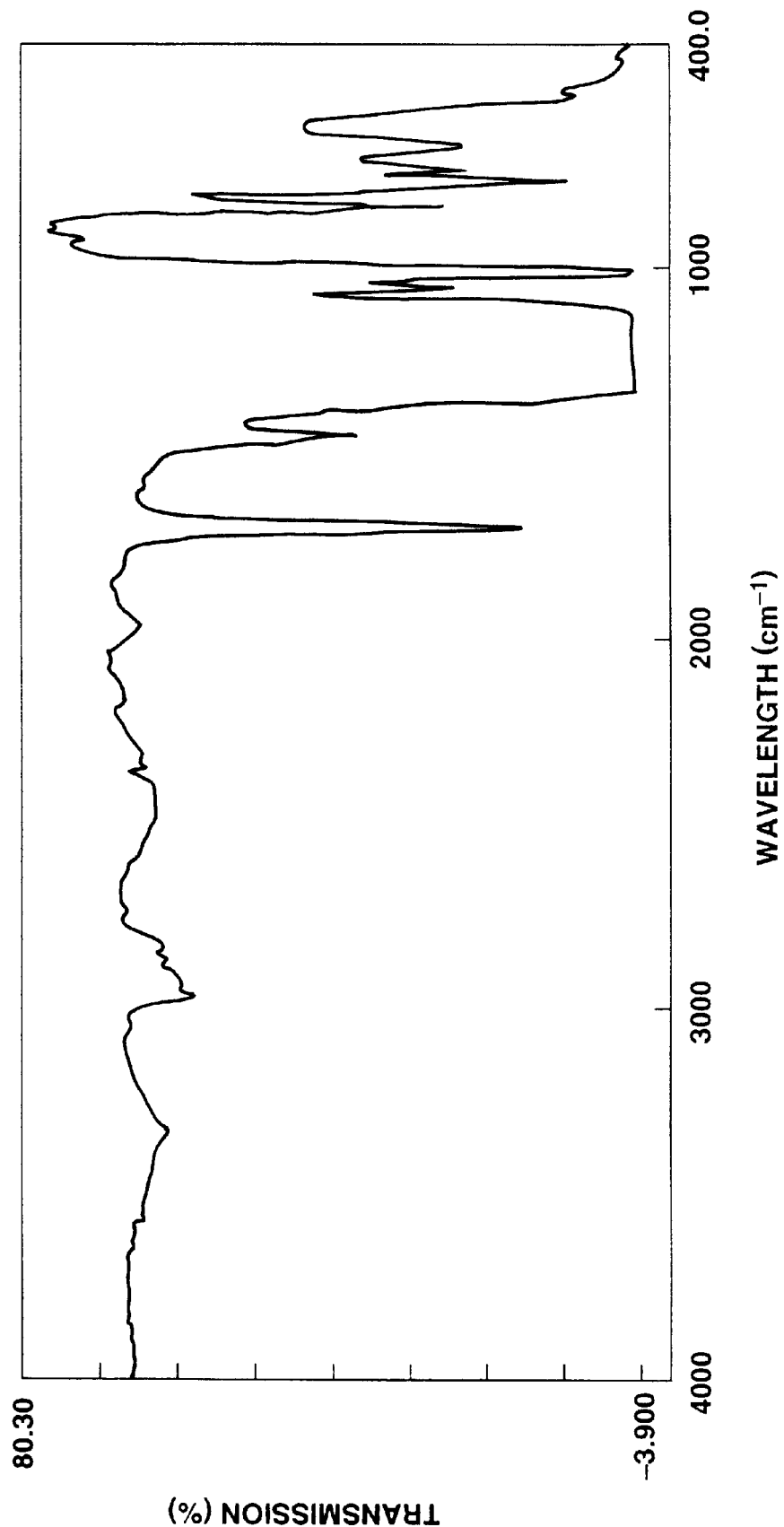
FIG. 2 shows an IR spectrum of the product of Example 2.

This compound had a viscosity of 2,800 cs at 25° C. and a refractive index of 1.3154 at 25° C. The IR spectrum of this compound is shown in FIG. 2, from which the following absorption was confirmed.

| | |
|---|---|
| 1100 to 1350 cm$^{-1}$ | vC—F |
| 1700 cm$^{-1}$ | vC=O |

The functional group equivalent weight of this compound was quantitatively determined and found to be 4,120 g/mol, thereby confirming the compound to be a polymer of the fluorinated amide compound having structural formula (10) below.

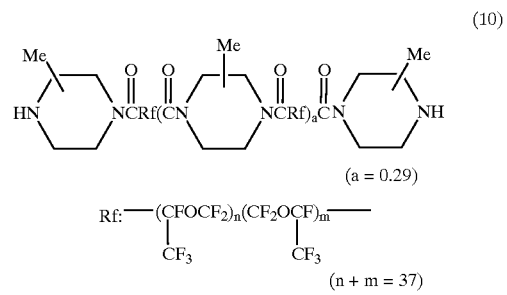

(10)

(a = 0.29)

(n + m = 37)

Example 3

Figure 3:
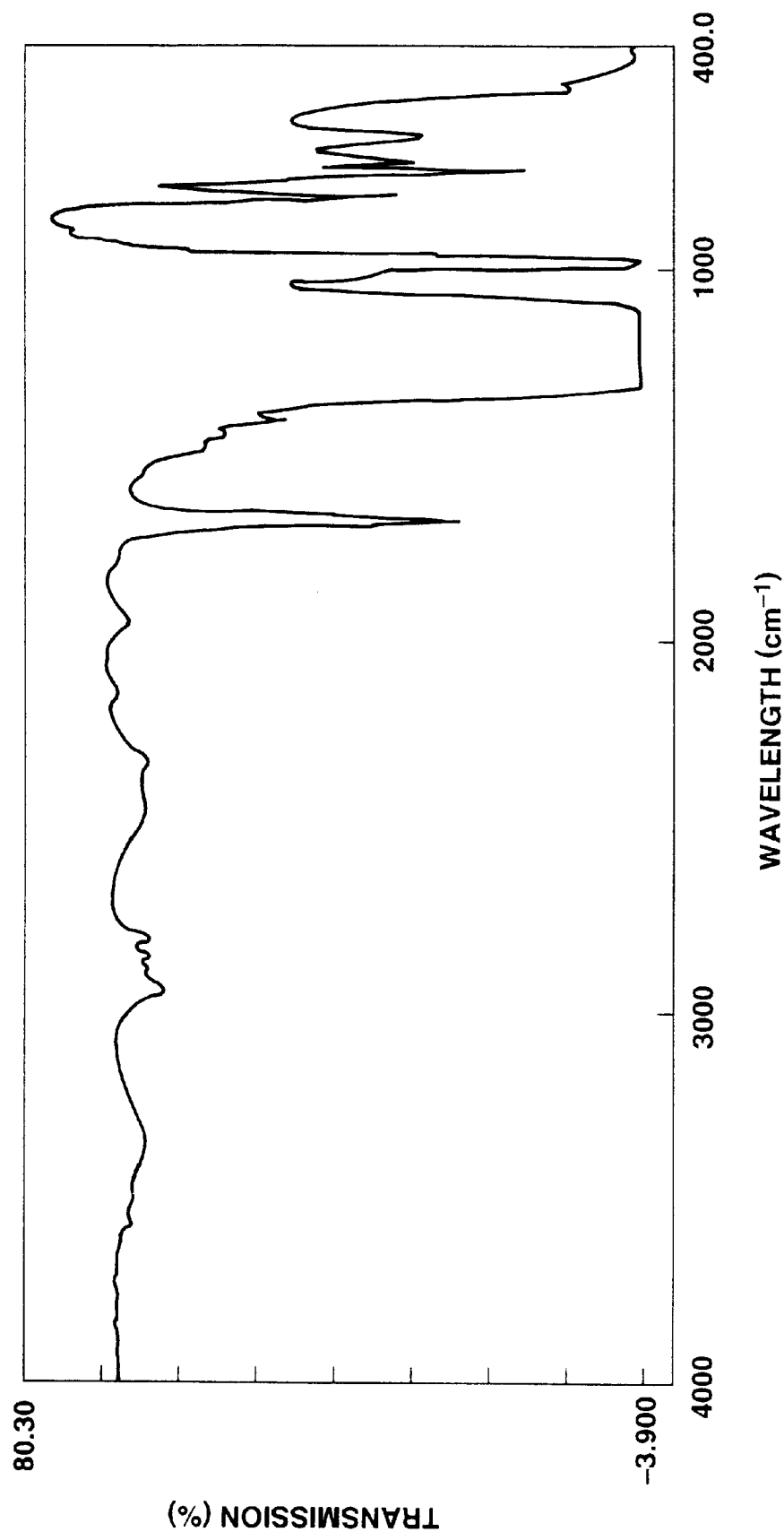
FIG. 3 shows an IR spectrum of the product of Example 3.

N,Ni-Dimethylethylenediamine (39 g) and 500 g of 1,3-bistrifluoromethylbenzene were charged into a 2-liter, four-necked flask fitted with a stirrer, a thermometer, a Dimroth condenser, and a dropping funnel, following which the temperature was raised to 80° C. under stirring. A mixture of 460 g of the compound with acid fluoride groups at both ends represented by formula (9) above and 500 g of 1,3-bistrifluoromethylbenzene was then added dropwise from the dropping funnel at a temperature of 80 to 90° C. After addition, the reaction was carried out at 80° C. for 2 hours. The resulting reaction product was washed with water to remove salts and excess N,Ni-dimethylethylenediamine. The organic phase was separated off, then vacuum stripped at 100° C. and 3 mmHg, giving 424.6 g of a clear, light-yellow liquid compound. This compound had a viscosity of 3,456 cs at 25° C. and a refractive index of 1.3121 at 25° C. The IR spectrum of this compound is shown in FIG. 3, from which the following absorption was confirmed.

| | |
|---|---|
| 1100 to 1350 cm$^{-1}$ | vC—F |
| 1700 cm$^{-1}$ | vC=O |

The functional group equivalent weight of this compound was quantitatively determined and found to be 5,460 g/mol, thereby confirming the compound to be a polymer of the fluorinated amide compound having structural formula (11) below.

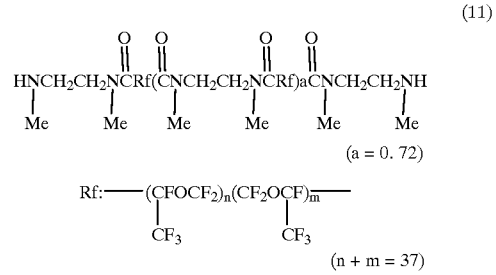

(11)

(a = 0.72)

(n + m = 37)

Japanese Patent Application No. 275022/1997 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

We claim:
1. A fluorinated amide compound of general formula (1):
(1)
wherein Rf is a divalent perfluoropolyether group, and X is a group represented by general formula (2):
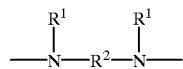
(2)
wherein $R^1$ is a substituted or unsubstituted monovalent hydrocarbon group, and $R^2$ is a substituted or unsubstituted divalent hydrocarbon group; and the letter m is an integer inclusive of 0.
* * * * *